United States Patent
Buss (10) Patent No.: US 7,588,732 B2
(45) Date of Patent: Sep. 15, 2009

(54) AUTOLOGUS TISSUE HARVESTING AND IRRIGATION DEVICE

(75) Inventor: Brian Buss, Plano, TX (US)

(73) Assignee: Genesis Biosystems, Inc., Lewisville, TX (US)

( * ) Notice: Subject to any disclaimer, the term of this patent is extended or adjusted under 35 U.S.C. 154(b) by 535 days.

(21) Appl. No.: 11/090,333

(22) Filed: Mar. 25, 2005

(65) Prior Publication Data

US 2006/0093527 A1    May 4, 2006

Related U.S. Application Data

(60) Provisional application No. 60/557,568, filed on Mar. 30, 2004.

(51) Int. Cl.
*B01L 11/00*   (2006.01)
*C12M 1/12*   (2006.01)
*A61M 5/00*   (2006.01)

(52) U.S. Cl. .................. 422/101; 210/94; 210/406; 210/416.1; 210/437; 210/451; 210/483; 210/484; 422/102; 422/104; 435/297.1; 435/297.2; 436/174; 436/177; 436/178; 604/121; 604/190; 604/234; 604/317; 604/406

(58) Field of Classification Search ............... 210/94, 210/209, 252, 257.1, 257.2, 258, 321.6, 321.78, 210/321.87, 348, 350, 406, 413, 416.1, 436, 210/437, 441, 451, 453, 454, 472, 483, 484, 210/497.01, 500.21; 435/288.6, 295.3, 297.1, 435/297.2; 436/174, 177, 178; 604/6.09, 604/6.11, 6.12, 35, 121, 141, 190, 234, 241, 604/540, 541, 542, 543, 544, 317, 319, 406; 422/101, 102, 104
See application file for complete search history.

(56) References Cited

U.S. PATENT DOCUMENTS

| | | | |
|---|---|---|---|
| 4,834,703 A * | 5/1989 | Dubrul et al. ................. 604/48 |
| 5,035,708 A | 7/1991 | Alchas et al. |
| 5,049,146 A * | 9/1991 | Bringham et al. .......... 604/6.09 |
| 5,352,410 A * | 10/1994 | Hansen et al. ................ 422/58 |
| 5,603,845 A * | 2/1997 | Holm ........................ 210/782 |
| 5,976,470 A * | 11/1999 | Maiefski et al. ............. 422/103 |
| 6,315,756 B1 | 11/2001 | Tankovich |
| 6,623,733 B1* | 9/2003 | Hossainy et al. ......... 424/93.21 |
| 2005/0084961 A1* | 4/2005 | Hedrick et al. .............. 435/366 |

* cited by examiner

*Primary Examiner*—John Kim
(74) *Attorney, Agent, or Firm*—Edwin S. Flores; Daniel J. Chalker; Chalker Flores, LLP (57) ABSTRACT

The present invention includes a harvesting and irrigation device, a method and a kit for the collection of viable fat cells and/or adipose tissue with decreased handing and improved yield and viability.

20 Claims, 4 Drawing Sheets

AUTOLOGUS TISSUE HARVESTING AND IRRIGATION DEVICE

CROSS-REFERENCE TO RELATED APPLICATIONS

This application claims priority to U.S. Provisional Patent Application Ser. No. 60/557,568, filed Mar. 30, 2004, hereby incorporated in its entirety by reference.

TECHNICAL FIELD OF THE INVENTION

The present invention relates in general to the field of tissue harvesting and, more particularly, to a device and method for the isolation and preparation of fatty cells for cell and tissue transplant.

BACKGROUND OF THE INVENTION

Without limiting the scope of the invention, its background is described in connection with the removal and re-insertion of autologous cells during reconstructive surgery.

Liposuction is a procedure for removing fatty tissue from the body in which a cannula is inserted and fatty tissue is removed by moving the cannula back and forth. Generally, the cannula is attached to a syringe or a vacuum pump that provide suction to remove broken-up fatty tissue. Liposuction devices are designed typically to withstand the temperatures and pressures of autoclaves for reuse in multiple procedures. Liposuction devices capable of multiple uses, however, increase greatly the unit cost. An alternative is to prepare single-use, disposable liposuction units.

A problem with the prior art is that these devices tend to generate large amounts of unusable material as the fatty tissue undergoes multiple-processes steps prior to re-introduction back into the host at an alternative site, e.g., during reconstructive surgery. The advantage of re-introducing autologous fatty tissue is that it reduces greatly or eliminates rejection of the tissue. Fatty tissue degradation is the result of a number of factors including, e.g., the delicate nature of the cells, the mechanical removal of the cells, the multiple step process used to separate viable cells from cell and tissue debris, the length of time the cells are ex vivo and the temperature and nature of the media in which the cells are extracted.

Current procedures use a multi-stage approach to remove cells from fatty tissue. To isolate fatty cells, the cells are extracted mechanically with and through a cannula from the liposuction site and are drawn into the lumen of, e.g., a 5 or 10 ml syringe. Vacuum pressure to the cells is provided by pulling the syringe plunger. Next, the cannula is removed and the entire syringe is fitted with, e.g., a specialized luer-lock® attachment with a rounded surface opposite the attachment point that provides a rounded surface for insertion into, and centrifugation by, a centrifuge. The cells are then centrifuged and the viable cells are isolated from within the lumen of the syringe by transferring the cells from the syringe used for removal into a re-insertion syringe. In addition, one or more centrifugation and/or wash steps may be included before re-insertion of the fatty cells.

Accordingly, there is a need for a disposable liposuction device and method that provides for decreased cost of fabrication necessary to justify using the device for just one procedure. The device must also be easy to use with current surgical equipment, methods and techniques, reduce the ex vivo time of the cells and reduce the handling and transfer of cells between vessels. Finally, the device must provide a higher percentage of viable cells for transfer, reduction in the amount of cellular debris and provide easy visualization of the status of the tissue and cells.

SUMMARY OF THE INVENTION

The present invention relates to a disposable liposuction device and method of use of a cell harvesting and irrigation device that provides improved fatty tissue quality for re-implantation. Using the device and method of the present invention improved cell viability is obtained due to reduced handling of the cells, e.g., eliminating the centrifugation, excess handling and extended exposure of cells to ambient air.

More particularly, the present invention includes a cell harvesting and/or irrigation device and kit having a housing, a filter chamber assembly disposed within the housing and a plunger tube (or assembly) within the filter chamber assembly. The filter chamber assembly may include a proximal filter support, a filter chamber and a distal chamber support and even be of unitary construction. Generally, a portion of the filter chamber assembly will be made of a porous material, e.g., having a porosity of about 120 to 220, with about 180 microns being particularly useful. The present invention may be attached to cannulas that are available currently and used with known techniques and methods without the need for new equipment in the surgical theater.

The housing, filter assembly and plunger tube may be made of a generally translucent material, may include marking and the like. The size of the housing may be 1 ml, 5 ml, 10 ml, 20 ml, 25 ml, 30 ml, 50 ml, 60 ml or even 100 ml. In some circumstances larger or even smaller sizes may be used depending on the amount of tissue to be collected and the harvest site or host. The plunger tube may include a proximal and a distal end, and a plunger attached to a proximal end of the plunger tube, and a vacuum attachment at the distal end of the plunger tube. The plunger may be opaque, e.g., colored, to be visible across the filter chamber and the housing. The plunger tube may be at least partially translucent and may even include markings of, e.g., volume.

The present invention also includes a method of harvesting and irrigating cells that includes the steps of collecting adipose tissue through a cannula or needle into the lumen of a housing that includes a filter chamber assembly disposed within the housing; and a plunger tube within the filter chamber assembly and connecting a vacuum to the plunger tube.

The invention disclosed herein has certain advantages over the prior art, including providing a sterile system or kit that is ready for office or operating room use. As the fat cells are collected in a single step, the harvested cells are maintained in a single enclosed sterile field. Other advantages of the harvesting device disclosed herein include a reduction in undesirable fluids while harvesting, it eliminates the need to centrifuge and then pour-off and/or wick-off the undesirable excess fluids and the harvested fat can be washed with a preferred or custom solution prepared specifically for a particular patient and application. Furthermore, by simply placing the harvest cannula into the solution (or loading a syringe connected using the transfer adapter), the washing solution will be drawn through the harvested fat and aspirated away. Also, harvesting is performed under a controllable and consistent vacuum level set by the user. By providing a conical tip design for the harvesting syringe and the large bore transfer adaptor, there is a marked reduction in fat cell damage while transferring to the injection syringe. As a result of these designs it has been found that the harvested fat looks cleaner, is oil-free, is more intact and more concentrated than other fat harvesting methods. Finally, by using a an aspirator that is powered continuously, LIPIVAGE™ can use a Mercedesstyle multi-hole cannula because the fluid is continuously removed while the fat collects in the filter chamber.

Using the present invention, it was possible to obtain fat cells that are natural and autologous and that are readily available for transfer in an ample supply. By harvesting a patient's own cells, there is no need for testing or allergic reaction concerns or requirements. The harvested and washed cells are the human-derived, potentially permanent filler. In fact, by transferring the patient's own cells, there is a natural look after injection. Unlike other filler, the transferred fat cells may be massaged after injection or even stored and used for correction at later time.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "lipocytes" is used to describe fat cells. These are related to, and form part of, adipose tissue, which are connective collagenous fibers with fat cells, fat cell materials and other tissue components.

Another term used herein is an "aspirator" that is connected to or is a pump for creating vacuum to use for removing unwanted blood, fluids or materials from the operative site. In order to maintain sterility and/or maximize cleanliness the device is connected to one or more waste canisters, often called "Bemis" containers. The waste containers act as traps for collecting unwanted fluids before they get to the aspirator pump; they are filtered and have overflow protection; they can be disposable and/or sterilized prior to disposal; and may have multiple ports for multiple or various instrument attachments.

In order to control the vacuum in the device, one or more regulators may be installed between the vacuum supply, the waste container and/or between the waste container and the device to control and meter for vacuum setting, usually a knob that is turned to control vacuum level.

As used herein, the term "cannula" is used to describe a long, rigid tube that is often larger than a hypodermic needle. One example of a cannula is an aspiration cannula, which is usually blunt-tipped and has at least one opening near tip with greater than 2 mm diameter, often used for taking tissue out of body. Another type of cannula is an "injection cannula," which is usually blunt tipped with small opening at tip area for delivering tissue to desired site. Cannulas are often attached to syringes at a luer, which is a fitting that insures good seal between most cannula and syringe, and more particularly with the device and system used with the LIPIVAGE™ harvester and method of the present invention. Typically, the luer threads are used for locking cannula more securely to the syringe.

As used herein, the term "tumescent" is used to describe a fluid injected to deliver, e.g., Epinephrine and Lidocaine to the area for harvesting and to replace fluids that are removed during liposuction and harvesting. Epinephrine (EPI) is generally provided as a small portion of the tumescent fluid and constricts blood vessels and helps limit loss of blood during liposuction as well as low volume harvesting. Lidocaine is also a small portion of the tumescent fluid and it helps reduce pain and inflammation at harvest site. Also used at injection site as well.

Other examples of tumescent solutions are well known in the art and may be used with the present invention. Of course, materials will be selected for the manufacture of the harvesting device of the present invention that are compatible with the fluids that will be handled. One example of a tumescent fluid that may be used with the present invention is taught in U.S. Pat. No. 6,315,756 issued to Tankovich, which teaches a tumescence fluid that includes perfluorocarbons and methods of using these compositions for subcutaneous fat removal. The composition contains a local anesthetic and/or vasoconstrictors, which may be associated with one or more pharmaceutical carriers.

Extraction site tumescence. Typically, a site will be prepared 15 to 30 minutes prior to harvesting by injecting saline or Ringers solution with traces of epinephrine and lidocaine. The volume injected varies between 10 cc and 500 cc depending on the surgeon. Generally, injecting 100 cc of wetting solution per site is recommended. A volume greater than 500 cc is possible, but not usually necessary. This wetting solution is sufficient for simultaneously washing the oil out of the fat while the fat is collecting inside the filter chamber of the harvester. Oil is an irritant and is important to remove prior to re-injecting the fat. Fat harvested and properly drained using LIPIVAGE™ has no oil component as is evident when left to stand and separate for ½ hour prior to re-injection, which is of great advantage during processing.

Setup. First, remove and retain the transfer adapter attached to the luer-lock tip of harvester. Connect LIPIVAGE™ tubing to the appropriate waste canister port. ⅜ inch tubing supplied may have to be adapted to larger port on waste canister using a ½ inch short piece of non-sterile tubing which will fit the larger port on the canister and will also fit snuggly over the ⅜ inch tubing of the LIPIVAGE™ kit. With LIPIVAGE™ connected, set the vacuum level of the aspirator to 18 in Hg (46 cm Hg, 460 mm Hg or 60.8 kpascal). If no meter is present or the scale on the meter is insufficient to determine the level, then set the vacuum adjustment to between 75 and 100%. Attach only a harvesting cannula and check the opening at the tip of the cannula for suction.

Harvest while washing simultaneously the fat and fat cells. Generally, this step will often include an assistant giving the doctor a 1 minute elapsed time callout. With the plunger in the same position as provided in the sterile pouch (about 1 cm from fully retracted position), begin harvesting for 1 minute. When completed with 1 minute of harvesting, the device is held upright and the plunger is pushed back slightly to a fully retracted position to quickly drain all fluids. Moving the plunger up and down slightly (less than 1 cm) will help drain the fluids as well. Draining the fluid takes about 10 seconds typically.

Transfer Concentrated Fat. Turn off the suction, detach the cannula from the harvester and attach the transfer adapter to the LIPIVAGE™ harvester. Next, remove the plunger from a chosen transfer syringe (not supplied with LIPIVAGE™ kit) and attach the syringe body to the LIPIVAGE™ harvester via the adapter. If transferring into 1 cc syringes, injecting into the back of the syringe leaving 0.1 cc at tip unfilled, works very well. Slowly push the LIPIVAGE™ plunger forward transferring fat to the attached syringe. Pull back slightly if resistance is encountered due to a clog developing during the transfer. When all fat is transferred to the transfer syringes, turn the vacuum on and clean the filter wall by using the LIPIVAGE™ plunger to wipe the entire length of the inner filter wall several times before the next harvest.

Commonly, collection of the desired adipose tissue involves the use of a suction pump connected to a collection apparatus that is connected to or fitted with a needle or cannula. For example, U.S. Pat. Nos. 5,035,708 and 4,834,703, relevant portions related to general adipose removal techniques are incorporated herein by reference, disclose the collection of adipose tissue using a suction pump to provide the necessary vacuum. However, it was found that such collection devices and associated methods tend to employ strong, uncontrollable suction that is extremely rough on the microvascular cellular components of the collected tissue. The resulting disruption of the relatively fragile cellular membranes can substantially lower the viability of the harvested cells. Disruption of the cellular membranes reduces dramatically the efficiency of the re-deposition process. While such collection procedures may provide sufficient adipose tissue, samples collected using such techniques generally require several additional labor-intensive preparatory and washing steps to assure an adequate concentration of relatively pure, viable cells for eventual deposition.

Further, source tissue collected using suction pumps is often relatively dirty, contaminated with unwanted body fluids, red blood cells, extracellular matrix components and other non-adipose cellular debris. Rather than obtaining translucent/white cell samples, as seen in relatively pure adipose tissue, samples collected using pump-generated vacuums often appear bloody, with concentrations of connective or membrane tissue dispersed within the fat and fat cells. The contaminants collected by these techniques require a series of handling and washing steps to prevent the contamination from interfering with transplant. Furthermore, if the tissue and/or cells are further processed washing, e.g., enzymes that improve the quality of the cells for grafting, such contaminants may inhibit the enzymatic activity of the proteolytic enzymes directly or indirectly, thereby leading to incomplete digestion of the sample and a corresponding reduction in the yield of non-adipose cellular components subsequently obtained by centrifugation. Furthermore, cells that are collected and centrifuged into pellets or plugs contain increased levels of non-endothelial components. The use of such contaminated pellets or plugs further lowers the efficiency of the cell deposition procedure and interferes with the efficiency of the graft. Consequently, the patient may have to endure more extensive liposuction than would otherwise be required in order to provide a sufficient number of fatty cells and/or tissue.

As the efficiency of the removal process is lowered with each handling step, the importance of starting with a relatively clean sample is evident. That is, a small increase in the amount of contaminating materials initially collected can reduce dramatically the yield of viable cells available for deposition. In addition to increasing the amount of adipose tissue that must be collected, the reduction in cell viability due to cell handling and contaminating materials must be compensated for by a larger deposition volume, number of depositions and/or the addition of time consuming and efficiency reducing purification steps.

The present inventor recognized that a need exists to improve the yield of viable adipose cells recovered from adipose tissue collected from a patient preparatory to implantation. The present invention is a device and method for efficiently harvesting and irrigating adipose cells from blood cells, connective tissue, and other materials that are present in the extracted material to maximize the number of viable cells available for re-insertion, e.g., adipose cells. The present invention may also be used to extract, wash and re-insert a wide variety of cells from all tissues.

The present invention overcomes the problems associated with the variable suction provided by syringes and permits the use of available hospital or clinic vacuum in the collection process. Alternatively, fixed or variable pressure pumps may be used in the operating environment to maximize the surgeon's ability to freely maneuver the device in order to collect, wash and evaluate adipose tissue in a single harvesting and irrigation device with minimal handling of the cells, without the need for a centrifuge and with minimal exposure of the fragile adipose cells to the environment with minimal friction.

Materials. While a wide variety of materials may be used to make the components of the present invention, including the use of off the self syringes and luer locks, the components may be made by injection molding, blow molding, extrusion, compression molding, or any other molding process or combination of molding processes. The one or more components may be assembled either by hand, partially or fully automated. The syringe components may be made of plastic, polymers, rubber materials, metals, alloys, glass, quartz, ceramics and mixtures or combinations thereof. Examples of suitable plastics include synthetic resins that are transparent, lightweight, resistant to fracture, moldable and economical. Examples of thermoplastic resins for use with the present invention include, e.g., polypropylene, olyethylene; polyisoprene; polybutene; polymethylpentene-1; polybutadiene resin; polyolefin family resin such as cyclic polyolefin; olefin copolymer such as ethylene-α-olefin copolymer; vinyl chloride resin; polyvinyl alcohol; polyvinyl acetal; polyvinyl acetate; ethylene-vinyl acetate copolymer; polyvinylidene chloride; polystyrene; acrylic resin; polyester resin such as polyethylene terephthalate, polybutylene terephthalate, polyethylene naphthalate; polyamide, polysulfone, polycarbonate, polyether, and polyphenylene sulfide; and thermosetting resins, for example, epoxy resin, phenol resin, and polyurethane.

The materials used to mold the syringe and syringe components will depend on the pressures, volume and capacity in which the syringe are used and the type of solution or fluid to which the syringe will be exposed. The materials selected may take into account factors such as, number of uses, expense, refurbishment, sterility, manufacturing and engineering. Some materials are more stable and resistant to organic solvents and diluents, e.g., glass syringes; while syringes formed with other materials are sufficient for working with other solutions or fluids, in particular for short exposures to materials and/or vacuum or pressure. Generally, the syringe barrels will be substantially transparent so the solutions or fluids in the barrel cavity can be monitored with regard to the volume measuring indicia formed and depicted on the syringe barrel.

More particularly, the harvesting and irrigation apparatus is attached to the vacuum source without compromising the maneuverability of the collection tip. The pumps and/or vacuum source will be selected to allow precise, real-time control of the strength of the vacuum at the collection tip, making it easy to maintain constant, even harvesting of the desired source tissue. The improved collection of viable cells reduces patient morbidity by reducing, if so required, the amount of tissue extracted and the length of time that the patient is under anesthetic, whether local or systemic. The present invention also allows for more precise control of tissue harvesting, thereby decreasing the contaminant level of the samples, which increases the collection of adipose tissue that contains lower levels of contaminants. Furthermore, the present invention allows for in situ washing of cells, if required, without the need for centrifugation and multiple syringes and transfers between syringes.

The present invention provides the following advantages over prior art fat removal and transfer systems: (1) it eliminates need for a centrifuge; (2) it provides lower and more constant (gentler) vacuum than a standard syringe; (3) it permits oil removal while harvesting; (4) the fat is concentrated or condensed while harvesting without the need for additional handling steps or equipment; (5) it simplifies task of additional washing of fat if desired and the system allows for washes harvested fat while harvesting using, e.g., the pre-injected wetting solution present at the harvesting site and/or combinations of solutions with or without other active agents, salts, buffers, ion and the like.

Figure 1:
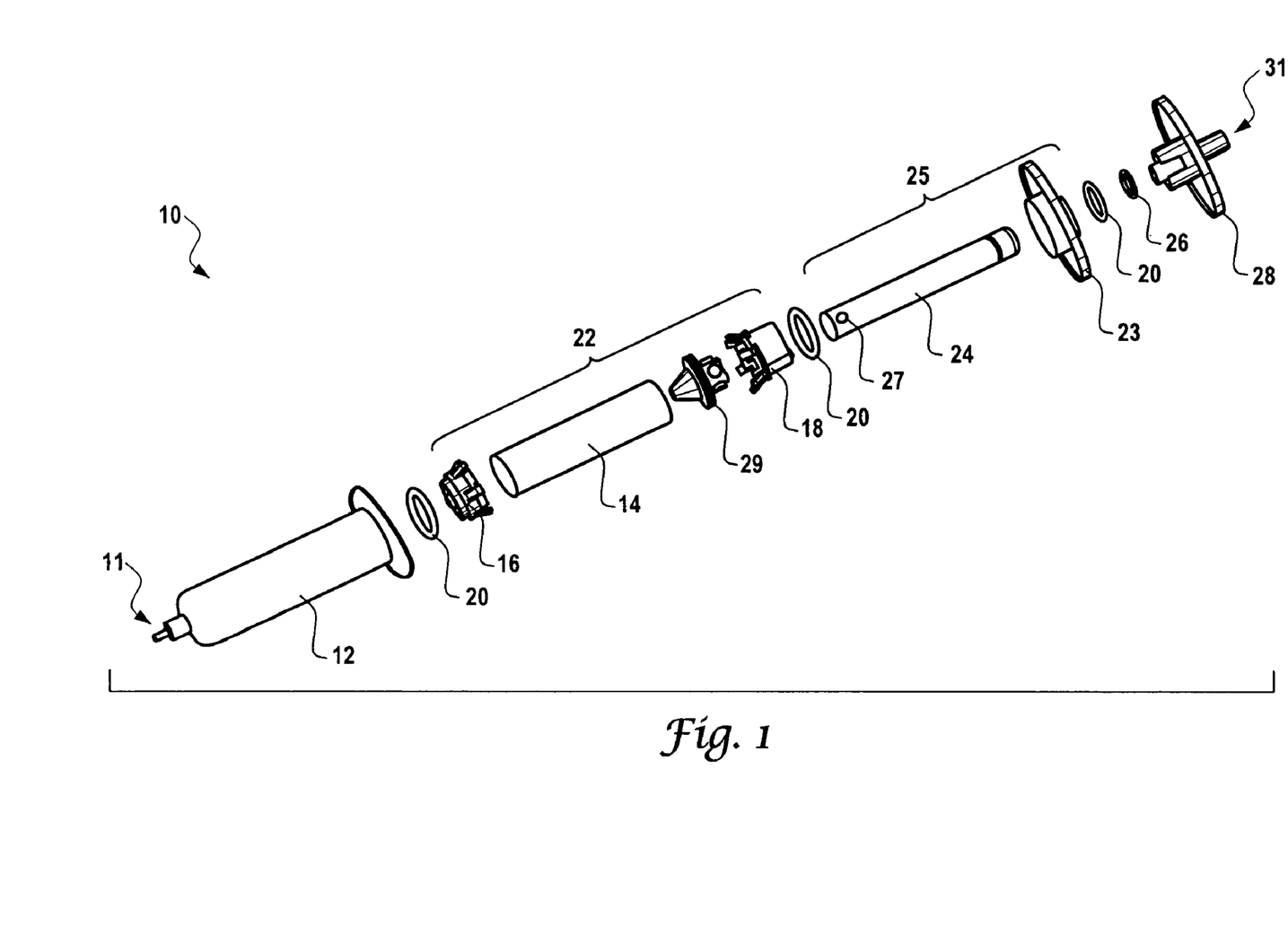
FIG. 1 is an expanded, isometric view of the tissue harvesting and irrigation device of the present invention.

FIG. 1 is an expanded, isometric view of the tissue harvesting and irrigation device 10 of the present invention. The device 10 includes a housing 12, into which a filter chamber 14 is introduced. Housing 12 may be an optically clear polymeric housing that allows the user to monitor the contents. Examples of polymeric materials include glass, quartz, plastic and the like. Generally, the housing 12 is open on both ends in order to accommodate assembly of internal components as well as to provide a portal 11 that allows entry of harvested tissue materials and washing fluids as well as exiting of unwanted components and fluids. The portal 11 allows attachment of the cannula (not shown) with an attachment that matched commercially available cannulas and needles, e.g., a Luek-Lock® attachment. The housing 12 provides an airtight chamber and barrier capable of providing vacuum or pressure capacity within its walls as well as containing fluids within. The shape depicted is cylindrical, however, other shapes and cross-sections may be used depending on the cannula used, the cross-section and surface area of the filter chamber required and the like, as will be apparent to the skilled artisan in light of the present disclosure The filter chamber 14 has, at least in part, a generally porous surface, e.g., 180 micron openings, and will be made of a biocompatible porous membranes, e.g., nylon, stainless steel, polyester and the like or combinations thereof. The filter chamber 14 depicted is tubular and mechanically supported at both ends within the housing 12. The diameter of the filter chamber 14 is less than the internal diameter of the housing 12 so that fluid may flow freely through the surface of the filter chamber 14 and along a space between the outer filter chamber 14 and the inner surface of the housing 12. The filter chamber 14 is suited for containing a majority of fat cells aspirated into the filter chamber 14 lumen, which is depicted as circular in shape. In operation, fluids to feed and/or wash the harvested cells are aspirated through the harvested material and out through the porous membrane by the vacuum allowing a washing process to occur while holding the desired tissues within the filter chamber 14 membrane. The shape is cylindrical but may be other shapes, volumes and/or sizes. The porosity and material as well as a multitude of layers or porosities may be used to process the same or other tissue types. For simplicity, the portal 11 will be described as the proximal end of the housing 12.

A filter chamber assembly 22 includes: the filter chamber 14, a proximal filter support 16 and a distal filter support 18. As depicted, the filter chamber 14 is supported in place within the housing 12 by the proximal filter support 16 and the distal filter support 18. The filter chamber assembly is located within the lumen of the housing 12 and a space is provided between the housing 12 and the filter chamber assembly 22. The distal filter support 18 may be a polymeric component (e.g., plastic, polymer, metal) that supports and fastens the filter chamber 14 membrane at the distal end of the harvester body. One or more o-rings 20 provide a seal between the filter chamber assembly 22 and the housing 12 in order to inhibit harvested tissue from going around the desired path from the cannula (not depicted) through the portal 11 into the space between the proximal filter support 16 of the filter chamber assembly 22 and the housing 12. A fluidic path is formed through the portal 11 of the housing 12 and the lumen of the filter chamber assembly 22. In one embodiment, the filter chamber assembly 22 is preassembled from different components, or is unimodular, that is, it is cast into as little as a single piece.

Figure 2:
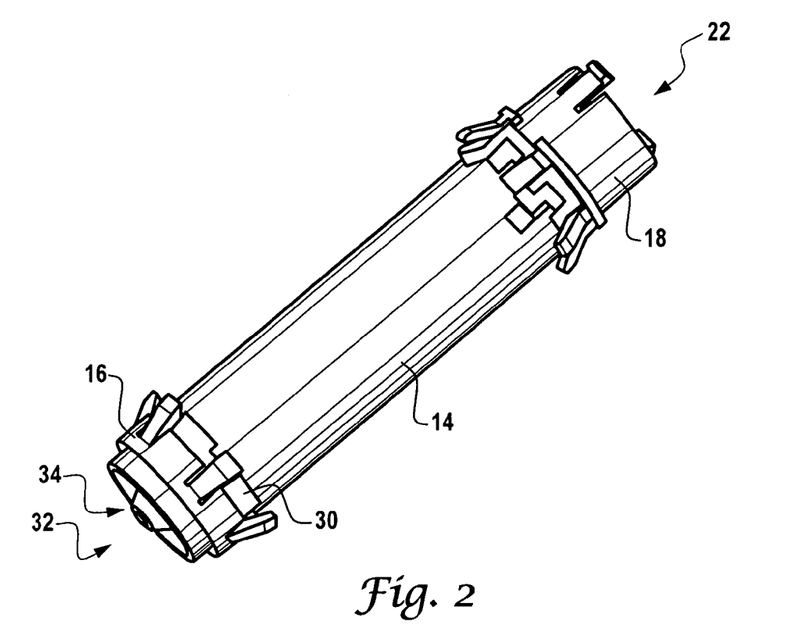
FIG. 2 is an isolated, isometric view of the filter chamber assembly.

As may be visualized in conjunction with FIG. 2, the proximal filter support 16 includes an opening 32 that is at or about the portal 11, and one or more openings or grooves 30 are provided around the outer surface of the proximal filter support 16 to permit a path for fluid between the portal 11 and the space outside the filter chamber assembly 22. The funnel shape 34 of the proximal filter support 16 serves as a channel allowing the material collected within the larger diameter of the filter chamber 14 to gradually transition to the smaller exit orifice diameter alleviating abrupt interfaces leading to back-pressure or clogging.

The distal filter support 18 may also be made of a polymeric material that supports and fastens the filter membrane of the filter chamber 14 at the distal end of the housing 12. The distal filter support 18 may also be support and/or accompanied by an external and internal seal using, e.g., o-rings 20. The external seal serves as the housing 12 seal allowing vacuum or pressure to be created within the lumen of the housing. The internal seal is dynamic in that the plunger 24 moves longitudinally against the inner seal 26. Both inner seal 22 and o-ring seal 20 serve to keep fluid within the housing 12 and produce a tight seal so that a vacuum source connected to the distal end of the plunger cap 28 can create the working vacuum and flow of air and fluids necessary to aspirate tissues and perform the washing processes. While the filter chamber assembly 22 is depicted as having several components, it may also be of unitary construction.

A housing cap 25 may also be made of a polymeric component. The housing cap 25 fastens mechanically the housing 12 and the distal filter support 18 in order to support the filter chamber assembly 22 within the lumen of the housing 12 from collapsing as well as to fasten onto and cap the distal opening of the housing 12. The housing cap 12 contains the filter chamber assembly 22 within the housing and is engineered so that normal plunger forces exerted by the user maintain the tissue harvesting and irrigation device 10 intact. The housing cap 25 also serves to contain the inner and outer seal of the proximal filter support so that they stay in place and provides a mechanical leverage point to push and pull the plunger assembly 25.

The plunger tube 24 may also be made of polymeric materials and includes an internal channel, lumen or duct as well as an outer surface that can be dynamically sealed against the inner seal 26. The plunger tube 24 is structurally strong enough to withstand the actuating forces of the plunger tube 24 in order to withdraw the plunger tip 29, along and within, the inner wall of the filter chamber 14 within the filter chamber assembly 22. The plunger tube 24 will generally be strong enough to push the harvested material (not depicted) out of the tissue harvesting and irrigation device 10. In this embodiment, a cylindrical shape is depicted, however, the skilled artisan will recognize that any number of shapes may be used depending on design parameters such as, e.g., surface area, volume, size of the porous openings in the membrane, target tissue, shape of the mating seal and the like without undue experimentation using the present disclosure.

The plunger tube 24 also serves as the retainer of the plunger tip 29 and includes at least vacuum opening 27. The plunger tube 24 fits within, and is generally co-axial with the filter chamber assembly 22 and provides an airtight channel for air and liquid to aspirate through to a vacuum source at the distal end of the plunger 24 from the vacuum opening 27, which allows for fluid communication between the lumen of the filter chamber assembly 22 and the lumen of the plunger tube 24 to a vacuum. A vacuum source is attached to the distal end of the plunger tube 24 opposite the plunger tip 25. Vacuum is delivered to the lumen of the housing 12 along the length of the airtight plunger tube 24. In the embodiment depicted, one or more openings are located that allow proximal to the plunger tip 25, the vacuum to draw air and liquids into the plunger and out of the harvester body and toward the vacuum source. The one or more plunger openings 27 are sized in order to provide adequate aspiration flow as well as to help avoid clogging. More than one port may be used for redundancy in case of a single port clog.

The plunger cap 28 includes a tubing interface 31 and may also be made of a polymeric material and provides the interface to a conduit, e.g., a flexible aspiration tubing (not depicted) and the plunger tube 24. The tubing interface 31 may be a tapered and allows the operator to place flexible tubing onto the port by securely expanding the internal diameter of the flexible tubing over the port outer diameter. The flange-portion of the plunger component provides the surfaces by which the user pulls back the plunger tube 14. The plunger cap 28 may be fastened mechanically onto the plunger tube 14 by, e.g., integrated latches and a groove provided at the distal end of the plunger tube 14. The seal to the plunger tube 14 may accomplished by making the unit from a single molded piece or may be two pieces that are connected using, e.g., an adhesive, a potting compound, an o-ring or other sealing mechanism. The flexible aspiration tubing that connects to the distal end of the plunger tube 14 (and the vacuum source) may be provided as part of a kit or may be provided separately, and will generally be a clear tube capable of withstanding a vacuum of between 2 and 30 mm of Hg, with 2, 5, 10, 15, 18 or 20 being useful vacuums. Alternatively, if a vacuum gauge is unavailable, the vacuum may be set at between about 25 to 100 percent vacuum, with 50 to 75 percent of the total vacuum setting providing a good starting point for harvest, evaluation and adjustment of the vacuum setting.

The plunger tip 29 will generally be made from an elastomeric material that is combines flexibility and mechanical strength, e.g., rubber or rubber-like. The plunger tip 29 is shaped to match the internal details of the proximal filter support 16 (e.g., conical) in order to purge harvested tissues more thoroughly from the lumen of the filter chamber assembly 22. The plunger tip 29 is also flexible in order to conform to the internal features of the filter chamber assembly 22, but it does not generally come in contact with the inner wall of the housing. That is, the plunger tip 29 will generally only exert mechanical pressure on the inner wall of the filter chamber assembly, in particular the filter chamber 14 and not generally to the inner wall of the housing 12. Certain embodiments may exist where the plunger tip 29 will mechanically come in contact with the inner wall of the housing 12 and are also encompassed herein. The outer flange(s) of the plunger tip 29 may be, e.g., flexible wipers whose diameters will generally exceed the inner diameter of the filter chamber 14. The distal portion of the plunger tip 29 may be equipped with bosses that fasten onto the plunger tube 14 and one or more channel(s) that allow for the plunger tube 14 plunger opening 27 to evacuate fluids and air proximal to the tip flange proximal filter support 16. The interfering surfaces with the inner walls of the filter chamber 14 allow for the harvested materials to remain largely on the proximal side of the plunger tip 29. The wiping action of the plunger tip 29 with the inner surface of the lumen of the chamber filter 14 also serves to keep the filter chamber 14 free of clogs in that tissue material that accumulates on the inner walls is wiped away by the plunger tip 29. The plunger tip 29 may be opaque or colored to make it visible through the housing 12 in order to be seen more clearly by the user, e.g., to monitor the position and amount of materials harvested within the filter chamber assembly 22. The o-rings 20 and inner o-ring 26 will generally be made of an elastomeric material. As with the polymeric, metallic or crystalline materials, the elastomeric materials will generally be made of biocompatible materials that are, e.g., light-weight, inexpensive, autoclavable or capable of being UV or gamma irradiated at least once.

Figure 3:
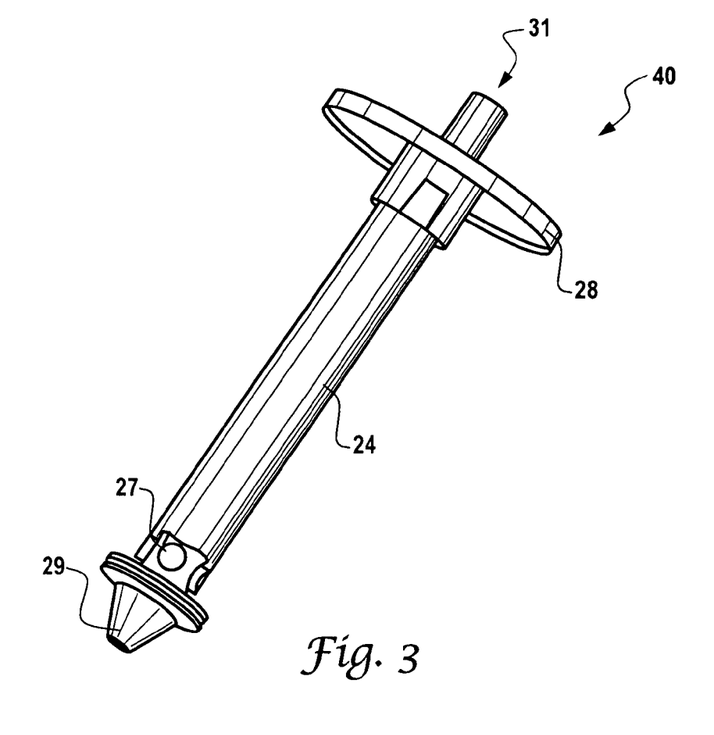
FIG. 3 is an isolated, isometric view of the plunger ant tip assembly.
Figure 4:
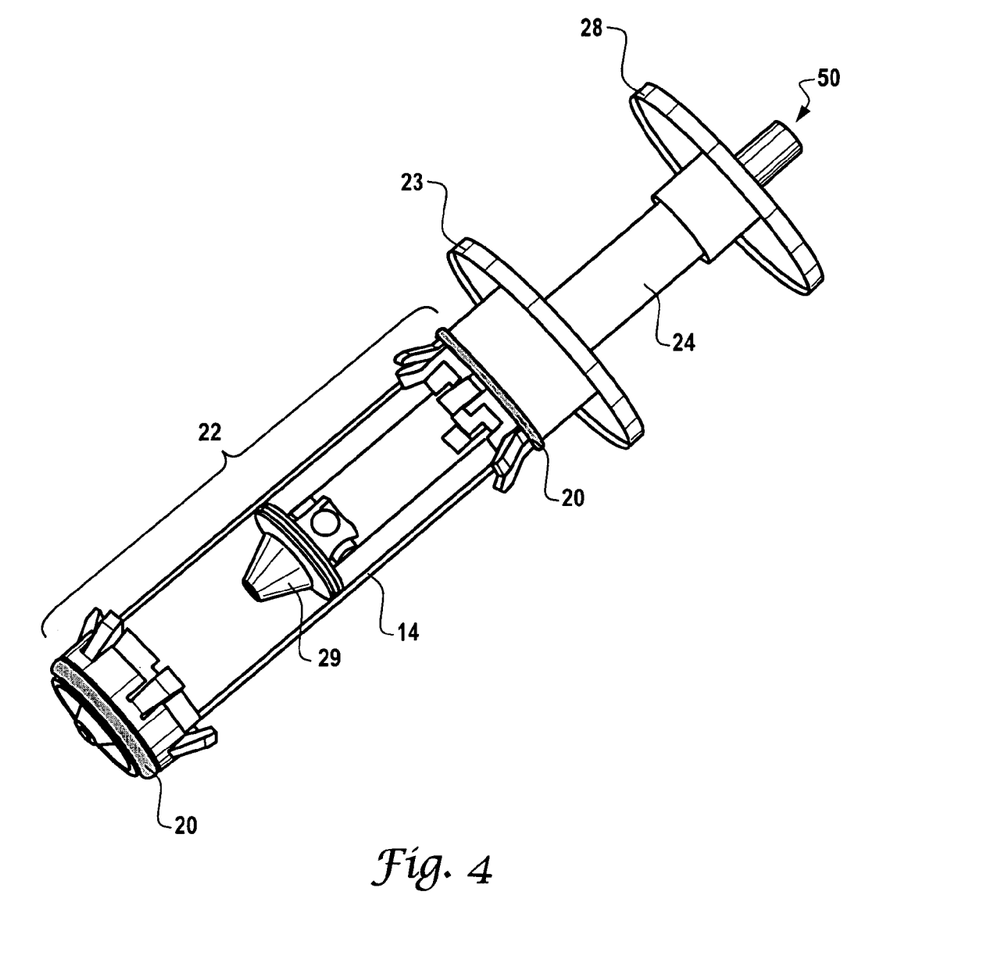
FIG. 4 is an isolated, isometric view of the harvester assembly than shows the interaction between the filter chamber assembly and the plunger and tip assembly.

FIG. 3 is an isolated, isometric view of the plunger tube assembly 40, which includes the plunger tip 29 attached to the plunger tube 24 connected to the plunger cap 28 and extends to the tubing interface 31 to vacuum opening 27. In operation, the plunger tip assembly 40 is inserted into the filter chamber assembly 22 (as shown in FIG. 4). Not depicted is another version of the plunger tip assemble 40 in which the assembly is cast into one or two parts, that is, the cap, tube and tubing interface are cast in a single piece or unit (with a vacuum opening) and the elastomeric tip is attached. The vacuum opening(s) may be varied in size depending on the strength of the vacuum, nature of the material being withdrawn and/or harvested (viscosity, percent fat, oils, site, source, etc), type of tumescent, size/volume of the overall assembly, etc. FIG. 4 is an isolated, isometric view of the primary harvester assembly 50 than shows the interaction between the filter chamber assembly 22, the plunger tube assembly 40 the plunger tip 29; and the housing cap 28.

Figure 5A:
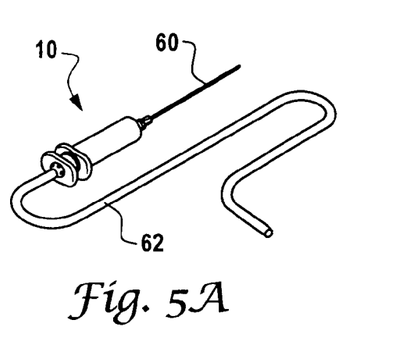
FIGS. 5A through 5E demonstrate the operation of the present invention.
Figure 5B:
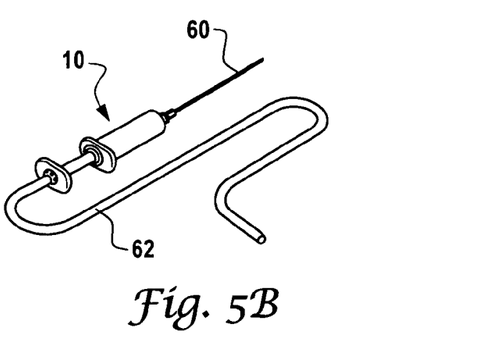

FIGS. 5A through 5E demonstrate the operation of the present invention. In operation, the harvesting and processing procedure begins with the attachment of the cannula 60 and the vacuum source 62. The cannula 60 is depicted here as attaching to the harvester and irrigation device 10 with a Luer-Lock® attachment point. In FIG. 5B the entire plunger assembly 64 is pulled from the housing 10. As depicted, the majority of the suction at the cannula is provided by the vacuum being drawn through the vacuum hose 62 and not due to the withdrawing the plunger.

Figure 5C:
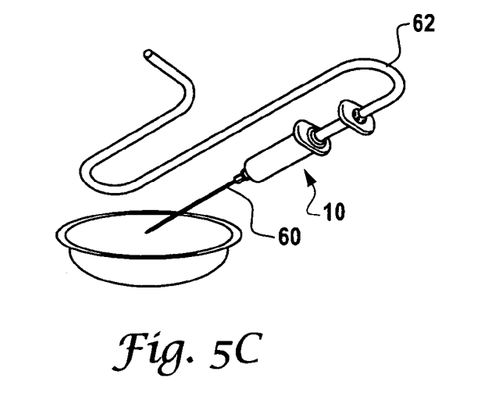
Figure 5D:
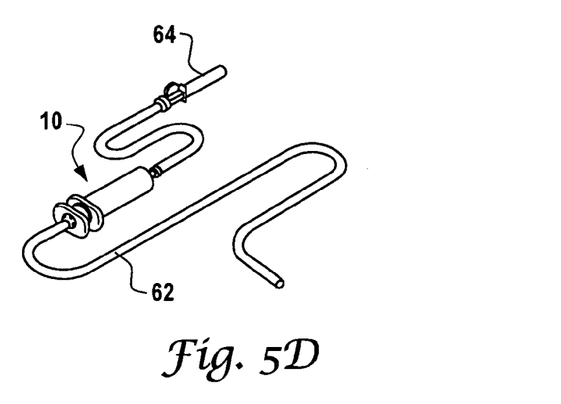
Figure 5E:
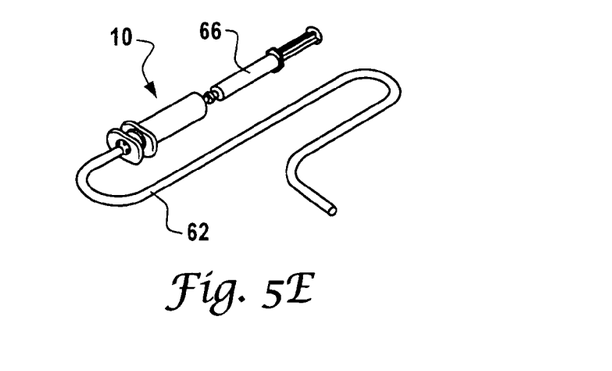

The lumen of the plunger tube 24 is exposed to the vacuum through the plunger tube opening 27 to the inner lumen of the filter chamber assembly 22 distal from the plunger tip 29, through the pores in the membrane that form the filter chamber 14, around the plunger tip 29 (and into the space between the filter chamber assembly 22 and the housing 12), back through the filter membrane 14 into the proximal lumen of the filter chamber 14, through the proximal filter support 16 into the lumen of the housing 12 at the portal 11 and into the lumen of the cannula 60. Cells are harvested through the cannula 60, past the portal 11 into the lumen of the filter chamber assembly 22 proximal from the plunger tip 29. As shown in FIG. 5C, the harvested cells may then be washed and/or allowed to soak in the presence of one or more buffering agents, enzymes, preservatives, growth factors and the like (FIG. 5D) and finally transferred into a second syringe 66 for delivery. Alternatively, and while generally not preferred, the vacuum may be reversed and the isolated and washed cells reinserted by delivering pressure into the device 10.

The use of the harvesting and irrigation device is described in the following example. First, the harvesting and irrigation device is placed inline between a vacuum source and the patient or tissue source. The vacuum source may be regulated and may also be provided via, e.g., a waste capture system composed of a vacuum canister with an integrated filter to prevent aspirant from flowing into the vacuum source. The patient or tissue source may be accessed via a cannula that is fastened mechanically and connected to the harvesting and irrigation device 10 or it may even be part of, and integrated with, the harvesting and irrigation device 10. The cannula may have a single or multiple port apertures near the tip, which allow the aspirant to be vacuumed into the inner channel of the cannula.

Next, the aspirant passes through the cannula and into the harvesting and irrigation device 10 via its proximal tip into the inner chamber of the filter chamber assembly 22 that may be suspended within the housing 12 of the harvesting and irrigation device 10. The inner chamber of the filter chamber 14 may be a generally tubular and porous, and is configured to capture adequately the aspirated fluids and tissues substantially within the filter chamber 14. The proximal and distal ends of the filter chamber assembly 22 are secured in order to retain the structure throughout the length and aid the containment of the aspirant. Both ends have an opening or channel that allows material within filter chamber 14 to be accessed. A plunger assembly 25 that has one or more openings along the long axis of the housing 12 provides a flexible interface between the plunger assembly 25 and the inner walls of the filter chamber assembly 22, which is achieved either by the filter chamber 14 being flexible or the plunger tip 29 being flexible and/or both. The proximal end of the plunger assembly 25 includes a plunger tip 29, one useful feature is that the plunger tip 29 is flexible and it interfaces with the lumen-side of the proximal filter support 16 such that it minimizes the dead volume within the lumen of the filter chamber assembly 22. By providing a plunger tip 29 that matches the proximal filter support 16, the reduction in dead space at the interface minimizes exposure to air and, importantly, turbulence about the plunger tip 29 at the interface between the proximal portion of the plunger tip and the tip seat on the distal face of the proximal filter support 16.

The plunger tube 24 includes one or more openings 27 that allow the plunger tube, which is hollow, to carry the fluids from the aspirant out from the distal end of the plunger that is equipped with a connection that allows for the sealing of aspirant tubing or conduit that is in turn connected to a vacuum source and/or waste canister. The plunger will generally move longitudinally, and concentric with and within the filter chamber 14, which is within the housing 12, and be sealed at the distal ends of the filter assembly 14 by o-ring 26. Once the entire plunger assembly 25 has been drawn from the filter chamber 14, thereby maximizing the volume of the proximal lumen of the filter chamber 12, the aspirant is largely held within the filter chamber 14.

The filter chamber 24 may include a single or varying degrees of porosity and allows fluid to flow through the harvested aspirant, through the pores to the outside of the filter chamber 14, around the plunger 29, into the space between the filter chamber 14 and the housing 12, back through the pores of the filter chamber 14 into the lumen distal from the plunger 29 into the opening(s) 27 in the plunger tube 24 and through the inner lumen of the plunger tube 24 and out of the device through a conduit attached to the tubing interface 31. The cross-sectional shape of the filter chamber 14 may be designed to maximize and/or minimize surface area, depending on the users needs, and may be, e.g., circular, oval, triangular, square, hexagonal, star-shaped and the like.

Flow may be controlled or even interrupted by an operator through both control of the vacuum level at the device and/or when withdrawing the plunger. Another advantage of the present invention is that harvested tissue may be seen through the chamber in order to observe the level of washing taking place. In general, blood is observed leaving the harvested material. In addition to (or instead of) washing with fluid, the clinician may irrigate or soak the harvested tissue within the chamber with some known or prescribed fluid mixture using, e.g., an external fluid source and access through the portal 11 to deliver fluid to the device. Vacuum may continue to be run with the harvesting and irrigation device 10 until the harvested tissue is processed, washed, fed sufficiently. The present device allows irrigation and/or washing so that the tissue may continue to purge fluids and also helps retain damaged cell material against the inside surfaces of the chamber due to the forces of the vacuum.

After the harvested tissue is sufficiently processed or washed, the tissue may be stored or dispensed. The tissue may be transferred into other containers or syringes. The plunger and tip moving proximal to distal inside the filter chamber is ejected or withdrawn from within the filter chamber 12 by harvesting the cells/tissue out of the proximal end of the device into a delivery site or another receptacle. A transfer conduit may be used to channel the ejected materials. The distal plunger tip 29 surface and the flexible fit against the plunger seat at the proximal filter support 16 acts upon the tissue pushing it forward until the tissue is sufficiently ejected. The flexible plunger tip 29 also conforms to the inner distal structure to minimize material left inside the filter chamber 14. The flexible plunger tip 29 also avoids dispensing some undesirable tissue material by wiping rather than scraping the inner filter chamber 14 walls by means of a flexible surface interface. The filter chamber 14 is wiped clean sufficiently enough to allow the porosity to continue to function beyond an initial harvesting iteration. As long as the porosity can be maintained the harvest and wash functions of the device remain intact.

The following is a description of a surgical procedure using the present invention. The harvesting and irrigation device is used as follows:

1) Open bag and remove sterile harvester with 12 foot tubing attached.

2) Attach end of tubing to aspiration source.
3) Adjust aspiration level to desired level, e.g., between about 10 to about 18 inches Hg.
4) Attach desired cannula with threaded luer-lock® connector (female) to the male threaded luer-lock® of the harvester.
5) Fasten cannula securely.
6) Check for vacuum at distal tip of cannula.
7) Retract plunger to desired position. For example, the ½ way point, however, the plunger may be fully retracted if desired.
8) Stab incision provides port for entry of the cannula.
9) Vacuum along with stroking motion in the sub-dermis region to provide fat and adipose tissue along with tumescent fluid and blood.
10) Continue harvesting until tip of cannula is clogged, chamber is full, desired amount has been removed and/or when flow of fluid through the chamber and waste tubing ceases.
11) Retract plunger or if already fully retracted push plunger forward until fat is noted at the tip of the cannula being ejected from the syringe. Harvest remains attached to vacuum source.
12) Pull plunger back again to allow more fat harvesting. Wiping action of plunger gently clears the stroked portion of the filter for better vacuum and washing to occur at the cannula tip.
13) Since fat is concentrating at the inner wall of the chamber, the inner region at the core is largely void. The plunger can be used to pack the harvested fat.
14) The gentle wiping action also allows the broken cell tissues to be more likely to be held in the filters pores and against the inside wall. The floating, lubricious, and suspended cells are more likely to stay suspended and as a result end up more highly concentrated with initially viable cells.
15) After harvesting and often during harvesting the doctor may irrigate the harvested fat in the chamber by submerging the tip of the cannula in washing solution.
16) After harvested fat is noted visually to be clean of red blood, with the vacuum still on, attach transfer syringes to harvester using the already attached transfer adapter fastened onto the transfer syringe. Firmly attach the transfer syringe to the harvester syringe.
17) Remove the plunger from the transfer syringe prior to filling. This removes the chance of building back pressure that may result in loss of fat from the transfer syringe once the syringes are disconnected.
18) After the transfer syringe is filled sufficiently by pushing on the plunger of the harvester which ejects the fat in the chamber even when still attached to the vacuum source, disconnect and replace the transfer syringe plunger being careful not to lose any transferred tissue.
19) Begin procedure again at Step 7.

Following a harvesting event, it may be useful to back-fill the site of fat cell removal with one or more temporary fillers. Non-limiting examples of temporary fillers include Restylane & Perlane—Hyaluronic Acid (QMED Esthetics); Zyderm I—3.5% bovine collagen (INAMED); Zyderm II—6.5% bovine collagen; Zyplast—3.5% bovine collagen cross linked with glutaraldehyde (INAMED); Cosmoderm/Cosmoplast—human collagen (INAMED); Radiance—calcium hydroxylapatite (Radiance); Autologen—3.5% Collagen yields 1 cc harvested from; patient 3 sq. in. skin harvest (COLLAGENESIS); Alloderm—freeze-dried human cadaver skin (LIFECELL); and Cymetra—injectable version of Alloderm. These temporary fillers have a varying degree of longevity, from between about 3, 6 to 12 months.

More specifically, the kit of the present invention may include one or more instruction booklets that teach one or more alternative uses and methods of harvesting viable fat cells for re-implantation. For example, these instructions may direct the user as follows:

1. Open flap of envelope in a non-sterile field. Carefully remove device and tubing from envelope without touching outer envelope surfaces. Contents are sterile.
2. Attach open end of tubing to appropriate vacuum or aspirator waste canister (not supplied). Tube fits over 6.5 mm to 8.5 mm tapered connectors (not supplied). Set Vacuum Level: Recommended to be 10 to 20 in. Hg or 254 to 508 mm Hg.
3. Detach the transfer adapter (retain for transfer of tissue) and attach the aspiration cannula (not supplied). Plunger should be retracted 75% or more within the device. Ensure vacuum suction at tip of cannula. Aspirate tissue from selected harvest site for approximately 60 seconds.
4. With plunger fully retracted, hold device upright to drain fluids for approximately 10 seconds. Move plunger slightly to aid drainage if needed.
5. Detach the cannula. Turn off the vacuum. Attach transfer adapter (may or may not be supplied). Connect a transfer syringe. Remove the plunger on the transfer syringe. Slowly push the LipiVage™ plunger forward to transfer the processed tissue to the syringe(s). Repeat until all tissue is transferred.
6. Turn the vacuum on. Use the plunger to wipe filter walls a few times. Optional: With the LipiVage™ plunger fully forward, place the LipiVage™ tip into washing solution to flush the filter.
7. To continue harvesting additional tissue, repeat steps 3 through 6 until the desired amount of tissue is harvested and transferred.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A cell harvesting device comprising:
   a housing comprising a portal located at a proximal end of the housing;
   a filter chamber assembly connected to the portal and disposed within the housing and having an exterior and an interior, wherein interior of the filter chamber assembly is in fluid communication with the portal;

a plunger tube slidably engaged within the filter chamber assembly, the plunger tube comprising a plunger at its proximal end, the plunger disposed within the filter chamber assembly, and wherein the plunger tube has one or more openings that allows fluid communication between the portal, the exterior of the filter chamber assembly and the interior of the plunger tube; and a tubing interface located at the distal end of the plunger tube.

2. The device of claim 1, wherein the filter chamber assembly comprises a proximal filter support, a filter chamber and a distal chamber support.

3. The device of claim 1, wherein the filter chamber assembly comprises a unitary construction.

4. The device of claim 1, wherein at least a portion of the filter chamber assembly comprises a porous material.

5. The device of claim 1, wherein at least a portion of the filter chamber assembly comprises a porous material with a porosity of between about 120 to 220 microns.

6. The device of claim 1, wherein at least a portion of the filter chamber assembly comprises a porous material with a porosity of around 180 microns.

7. The device of claim 1, wherein housing is generally translucent.

8. The device of claim 1, wherein the plunger tube comprises a proximal and a distal end, and wherein a plunger is attached to a proximal end of the plunger tube and the distal end of the plunger tube.

9. The device of claim 1, wherein the housing has a volume of about 1 ml, 5 ml, 10 ml, 20 ml, 25 ml, 30 ml, 50 ml, 60 ml or even 100 ml.

10. The device of claim 1, wherein the housing comprises plastic, polymers, rubber materials, metals, alloys, glass, quartz, ceramics and mixtures or combinations thereof.

11. The device of claim 1, wherein the housing and the plunger tube are capable of withstanding a vacuum of between 2 and 30 mm of Hg.

12. The device of claim 1, wherein the filter chamber assembly comprises a polymeric, a metallic, a crystalline material or combinations thereof.

13. The device of claim 1, wherein the plunger tube comprises elastomeric and biocompatible materials.

14. The device of claim 1, wherein the housing, the filter chamber and the plunger tube are light-weight, inexpensive, autoclavable or capable of being UV or gamma irradiated at least once.

15. A tissue harvesting device comprising:
a hollow cylindrical housing comprising a housing portal at a proximal end and a seal at the distal end, the housing having an inner diameter;
a cylindrical filter chamber in fluid communication with the housing portal and disposed coaxially within the housing, the filter chamber having an outer diameter that is less than the inner diameter of the housing;
a plunger assembly disposed within and coaxial with the filter chamber, the plunger assembly slidably engaged with the cylindrical filter chamber, comprising:
a plunger having the same outer diameter as the filter chamber but less than the inner diameter of the housing;
a hollow plunger attached to the plunger at a proximal end and a vacuum attachment at the distal end, wherein the hollow plunger is sealed at a seal housing; and
one or more openings in the hollow plunger;
wherein the housing portal, the filter chamber, the volume defined between the inner diameter of the housing and the external diameter of the filter chamber, the opening in the plunger assembly and the interior of the hollow plunger are in fluid communication.

16. The device of claim 1, wherein the filter chamber assembly comprises a unitary construction.

17. The device of claim 1, wherein at least a portion of the filter chamber assembly comprises a porous material with a porosity of between about 120 to 220 microns.

18. The device of claim 1, wherein at least a portion of the filter chamber assembly comprises a porous material with a porosity of around 180 microns.

19. The device of claim 1, wherein the housing has a volume of about 1 ml, 5 ml, 10 ml, 20 ml, 25 ml, 30 ml, 50 ml, 60 ml or even 100 ml.

20. The device of claim 1, wherein the housing comprises plastic, polymers, rubber materials, metals, alloys, glass, quartz, ceramics and mixtures or combinations thereof.

* * * * *

UNITED STATES PATENT AND TRADEMARK OFFICE
CERTIFICATE OF CORRECTION

PATENT NO.        : 7,588,732 B2
APPLICATION NO.   : 11/090333
DATED             : September 15, 2009
INVENTOR(S)       : Brian Buss It is certified that error appears in the above-identified patent and that said Letters Patent is hereby corrected as shown below:

Col. 1, line 35
Replace "multiple-processes steps" with --multiple-process steps--

Col. 1, line 64
Replace "time of the cells and" with --time of the cells, and--

Col. 3, line 24
Replace "plunger ant tip" with --plunger and tip--

Col. 15, line 23
Replace "wherein housing is" with --wherein the housing is--

Col. 16, line 27
Replace "The device of claim 1," with --The device of claim 15,--

Col. 16, line 29
Replace "The device of claim 1," with --The device of claim 15,--

Col. 16, line 32
Replace "The device of claim 1," with --The device of claim 15,--

Col. 16, line 36
Replace "The device of claim 1," with --The device of claim 15,--

UNITED STATES PATENT AND TRADEMARK OFFICE
CERTIFICATE OF CORRECTION

PATENT NO. : 7,588,732 B2
APPLICATION NO. : 11/090333
DATED : September 15, 2009
INVENTOR(S) : Brian Buss It is certified that error appears in the above-identified patent and that said Letters Patent is hereby corrected as shown below:

Col. 16, line 39
Replace "The device of claim 1," with --The device of claim 15,--

Signed and Sealed this

Twenty-ninth Day of December, 2009

David J. Kappos
*Director of the United States Patent and Trademark Office*